(12) United States Patent
Sella et al.

(10) Patent No.: US 9,375,523 B2
(45) Date of Patent: Jun. 28, 2016

(54) METHOD AND APPARATUS FOR CONTROLING FLOW RATES AND PATTERNS OF HUMAN MILK SECRETION BY A BREAST PUMP

(71) Applicant: VASA APPLIED TECHNOLOGIES LTD., Or Yehuda (IL)

(72) Inventors: Yoav Sella, Holon (IL); Yaakov Polgar, Holon (IL)

(73) Assignee: VASA APPLIED TECHNOLOGIES LTD, Or-Yehuda (IL)

( * ) Notice: Subject to any disclaimer, the term of this patent is extended or adjusted under 35 U.S.C. 154(b) by 23 days.

(21) Appl. No.: 14/347,271

(22) PCT Filed: Sep. 24, 2012

(86) PCT No.: PCT/IL2012/050387
§ 371 (c)(1),
(2) Date: Mar. 26, 2014

(87) PCT Pub. No.: WO2013/046206
PCT Pub. Date: Apr. 4, 2013

(65) Prior Publication Data
US 2014/0236079 A1    Aug. 21, 2014

Related U.S. Application Data

(60) Provisional application No. 61/539,134, filed on Sep. 26, 2011.

(51) Int. Cl.
*A61M 1/06*     (2006.01)
(52) U.S. Cl.
CPC ............... *A61M 1/062* (2014.02); *A61M 1/06* (2013.01); *A61M 2205/3334* (2013.01); *A61M 2205/3576* (2013.01); *A61M 2205/52* (2013.01)

(58) Field of Classification Search
CPC .......... G01N 30/32; G01N 30/52; A61M 1/06; A61M 1/062; A61M 1/068; A61M 2205/52; A61M 2205/3334
See application file for complete search history.

(56) References Cited

U.S. PATENT DOCUMENTS

| 5,571,084 | A | 11/1996 | Palmer | |
|---|---|---|---|---|
| 6,547,756 | B1 | 4/2003 | Greter et al. | |
| 2004/0024351 | A1 | 2/2004 | Greter et al. | |
| 2005/0101908 | A1* | 5/2005 | Atkin | A61M 1/06 604/74 |
| 2010/0016789 | A1* | 1/2010 | Bosshard | A61M 1/06 604/74 |

FOREIGN PATENT DOCUMENTS

| CN | 1683022 | 10/2005 |
|---|---|---|
| WO | WO 2008/127991 | 10/2008 |

(Continued)

OTHER PUBLICATIONS

Supplementary European Search Report of European Application No. 12835169 dated Apr. 21, 2015.

(Continued)

*Primary Examiner* — Bradley Osinski
(74) *Attorney, Agent, or Firm* — Pearl Cohen Zedek Latzer Baratz LLP

(57) ABSTRACT

The invention relates to an apparatus and method to control the flow rates and pattern of human milk secretion while using a breast pump. The apparatus comprises a breast pump having a linear source of vacuum and a communication port for communicating with an external source of information on milk flow rates and patterns of a breastfeeding baby, through an external control circuit.

12 Claims, 4 Drawing Sheets

(56) References Cited

FOREIGN PATENT DOCUMENTS

| | | |
|---|---|---|
| WO | WO 2010/096547 | 8/2010 |
| WO | WO 2011/117859 | 9/2011 |

OTHER PUBLICATIONS

Chinese Office Action of Chinese Application No. 2012800547120 mailed Aug. 3, 2015.

* cited by examiner

METHOD AND APPARATUS FOR CONTROLLING FLOW RATES AND PATTERNS OF HUMAN MILK SECRETION BY A BREAST PUMP

CROSS-REFERENCE TO RELATED APPLICATIONS

This application is a National Phase Application of PCT International Application No. PCT/IL2012/050387, International Filing Date Sep. 24, 2012, claiming priority of U.S. Patent Application No. 61/539,134, filed Sep. 26, 2011, which are hereby incorporated by reference.

FIELD OF THE INVENTION

The present invention relates to health care products and methods and more particularly to an apparatus and method to control the flow rates and pattern of human milk secretion while using a breast pump.

BACKGROUND

The mammary glands are a secreting organ of milk that is ideally suited to babies and the composition of which is ideally suited to the babies age.

The flow rate and pattern of the secreted milk changes as the baby grows, since the suction power and intensity of the suckling that he/she applies on the breast is changing. The flow rate and pattern can be measured as disclosed in WO2011117859, in the form of a device herein after referred to as a Nursing Meter Breast pump are used to remove milk from the breast, to be appropriately stored and used later on, by feeding the baby through e.g. a feeding bottle. Breastfeeding pumps available on the market, are divided into two main categories—Manual pumps and electric pumps.

More advanced electric pumps, usually hospital grade ones, include pressure and cycling control button/s, to reach a convenient pumping power and pattern. The pump's pumping power (vacuum value) is much greater than the vacuum generated by a suckling baby, and allows extraction of large amount of milk in a relatively short period of time. There are two main negative outcomes to that:

1) Using a pump causes excessive breast milk production, higher than the natural production rate, thus leading sometimes to congestion in the breasts.

2) Milk composition is naturally adapted to the age of the baby. Due to too high suction power of the pump, the breast "feels" as if the baby is older, thus changes the composition of milk to fit the age of this "mechanical baby", instead of the real baby's age.

EMBODIMENTS OF THE INVENTION

Embodiments of the present invention provide a device and a method of controlling the flow rates and pattern of human milk secretion while using a breast pump, to fit the baby's age and more particularly the specific baby being breastfed.

Embodiments of the present invention provides an apparatus for controlling the flow rate and pattern of human milk while using a breast pump, comprising:

a) a nursing meter that allows for measurement and recording of flow rates and suckling patterns generated by a breastfed baby, and further translation of the recorded flow rates and suckling pattern into a pumping power and pattern and the corresponding voltage values and pattern to operate the breast pump.

b) means for connecting the nursing meter to a breast pump, e.g., data and/or voltage connector, data and/or voltage cable In an exemplary embodiment, there is provided an apparatus comprised of a) a nursing meter that allows for measurement and recording of flow rates and suckling patterns generated by a breastfed baby, b) a separate control circuitry, connected to the nursing meter, that allows for translation of the recorded flow rates and suckling pattern into a pumping power and pattern and the corresponding voltage values and pattern to operate the breast pump; and c) means for connecting the control circuit to a breast pump, e.g., data and/or voltage connector, data and/or voltage cable In another exemplary embodiment, there is provided an apparatus comprised of a) a nursing meter that allows for measurement and recording of flow rates and suckling patterns generated by a breastfed baby, c) means for connecting the nursing meter to a breast pump, e.g., data and/or voltage connector, data and/or voltage cable and b) a control circuitry, provided within the breast pump, that allows for translation of the recorded flow rates and suckling pattern into a pumping power and pattern, to be generated by the pump and the corresponding voltage values and pattern to operate the pump.

DETAILED DESCRIPTION OF THE INVENTION

Figure 1A:
FIGS. 1a-1c are diagrammatic views of three exemplary embodiments of the apparatus according to the invention.

There is seen in FIG. 1a, an apparatus 10a for determining the flow rate and pattern of milk transferred from the breast to the nursed baby. The apparatus includes a control circuitry 12a that converts recorded data of flow rate and pattern to vacuum power and pattern of a breast pump. The apparatus is connected with a communication cable to a breast pump 14a.

Figure 1B:

There is seen in FIG. 1b, an apparatus 10 for determining the flow rate and pattern of milk transferred from the breast to the nursed baby. The apparatus is connected via a communication cable to a control circuitry 12 that converts recorded data of flow rate and pattern to vacuum power and pattern of a breast pump. The control circuit is further connected via a communication cable to a breast pump 14b.

Figure 1C:
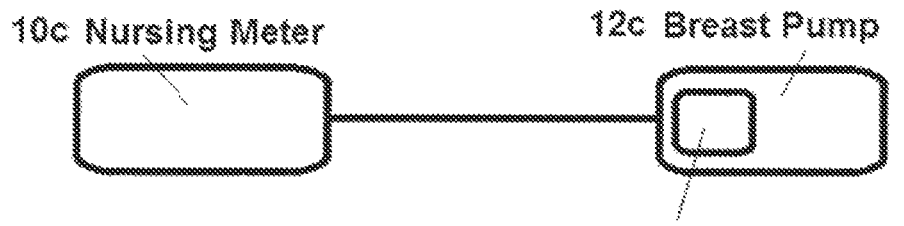

There is seen in FIG. 1c, an apparatus 10c for determining the flow rate and pattern of milk transferred from the breast to the nursed baby. The apparatus is connected via a communication cable to a control circuitry 12c that converts recorded data of flow rate and pattern to vacuum power and pattern of a breast pump. The control circuit is further connected via a communication cable to a breast pump 14c.

Figure 2:
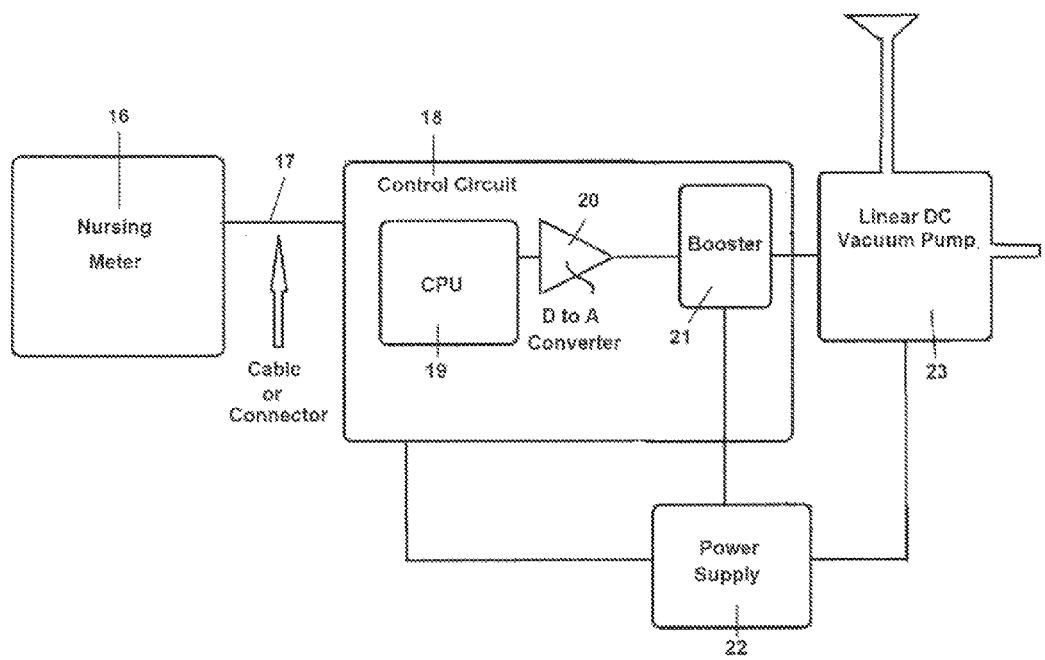
FIG. 2 is a diagram of a method create a conversion table between vacuum power and pattern of a breast pump and flow rate and pattern, and vice versa.

Referring now to FIG. 2, there is depicted diagrammatically a general control circuit 18, connected to a nursing meter 16 through a cable or connector 17, and to a linear breast pump 23 having a power supply 22. The control circuit 18 comprises of a controller (CPU) 19, a digital to analog signal converter 20 and a voltage booster 21. The controller 19 is preprogrammed with a communication protocol, allowing it to receive information from the nursing meter 16 and to convert it to corresponding voltage levels and pattern to be applied to the breast pump. The required voltage level and pattern is then transferred to the voltage booster 21, through the digital to analog signal converter 20. The required voltage level and pattern is realized by the voltage booster 21, and allow the breast pump to reach the required vacuum level and pattern, corresponding to the flow rate and pattern, received from the nursing meter 16.

Figure 3:
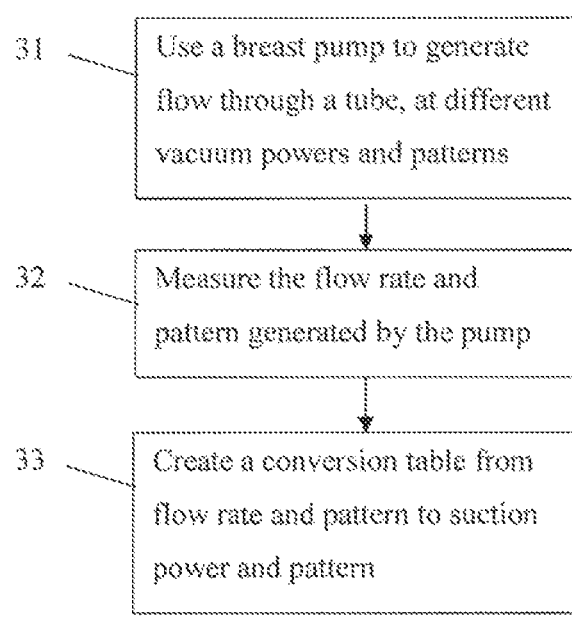
FIG. 3 is a diagram of a method for predetermining and creating a conversion table between vacuum power and pattern of a breast pump and flow rate and pattern.

Referring now to FIG. 3, there is depicted diagrammatically a method for pre determining and creating a conversion table between vacuum power and pattern of a breast pump and flow rate and pattern, and vice versa. The method may include:

Providing a breast pump 14a, 14b or 14c, to generate flow through a tube, at different vacuum powers and patterns [step 31].

Measuring the flow rates and patterns generated by the pump, at different vacuum powers and vacuum patterns [step 32].

Creating a conversion table from flow rate and pattern to suction power and pattern, and vice versa [step 33].

Figure 4:
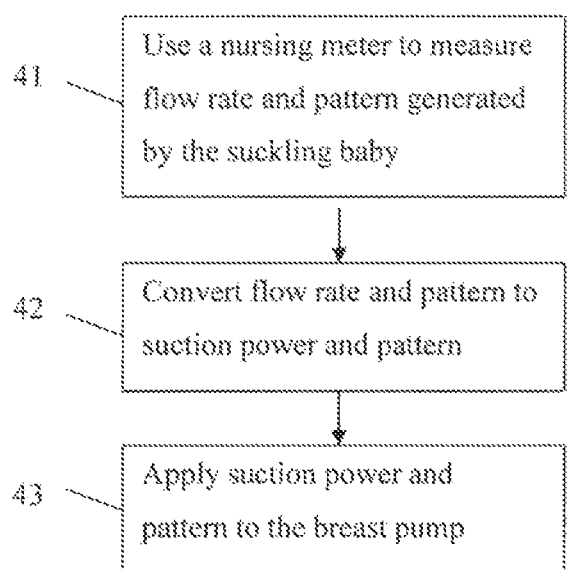
FIG. 4 is a diagram of a method of using recorded data of flow rate and pattern to vacuum power and pattern of a breast pump.

Referring now to FIG. 4, there is depicted diagrammatically a method for using recorded data of flow rate and pattern, as measured by the nursing meter, to vacuum power and pattern of a breast pump. The method may include:

Using a nursing meter to measure and record flow rates and patterns generated by the suckling baby [step 41].

Converting flow rate and pattern to suction power and pattern, based on the predetermined conversion table [step 42].

Applying suction power and pattern to the breast pump, corresponding to the converted data [step 43].

What is claimed is:

1. An apparatus for controlling flow rates and patterns of milk secretion comprising:
    a breast pump comprising a linear source of vacuum; and
    a control circuit comprising a controller for controlling the breast pump programmed to receive information on milk flow rates and patterns of a breastfeeding baby and to convert the information to corresponding voltage levels and patterns to be applied to the breast pump; and a nursing meter for determining and providing said information on flow rates and patterns.

2. The apparatus of claim 1 wherein said control circuit is located inside the breast pump.

3. The apparatus of claim 1 wherein said controller is arranged to control the operating voltage of the linear vacuum source, preprogrammed with a communication protocol allowing it to receive required operating voltage values and variation pattern, from a nursing meter, for achieving the required vacuum values and pattern;
    and wherein the control circuit further comprises a digital-to-analog signal converter; and
    a voltage booster to allow reaching the required voltage values.

4. The apparatus of claim 3 wherein said controller is preprogrammed with:
    a communication protocol allowing it to receive, from the nursing meter, the required said vacuum values and pattern; and
    data of the required said operating voltage values and variation pattern, to achieve the communicated vacuum values and pattern.

5. The apparatus of claim 3 wherein said controller is preprogrammed with:
    a communication protocol allowing it to receive, from the nursing meter, the required flow values and pattern, of the milk to be secreted by using the pump; and
    data of the required said operating voltage values and variation pattern, to achieve the communicated milk flow rate and pattern.

6. The apparatus according to claim 1 wherein said controller is programmed to perform said conversion based on a predetermined conversion table between vacuum power and pattern of a breast pump and flow rate and pattern.

7. A method for generating data to be stored in a controller of a control circuit of a breast pump comprising a linear source of vacuum, the method comprising:
    receiving from a nursing meter information on milk flow rate and pattern of breastfeeding babies;
    using the breast pump linear source of vacuum to generate flow through a tube at different vacuum powers and patterns;
    measuring the flow rate and pattern through the tube generated by the pump,
    creating a conversion table from flow rate and pattern through the tube to suction power and pattern of the pump.

8. The method according to claim 7
    wherein the controller for controlling the breast pump is programmed to receive information on milk flow rates and patterns of a breastfeeding baby and to convert the information to corresponding voltage levels and patterns to be applied to the breast pump.

9. The method according to claim 8 wherein said control circuit is located inside said breast pump.

10. A method of controlling the flow rate and pattern of human milk secretion while using a breast pump, the method comprising:
    using a nursing meter to measure flow rate and pattern generated by a suckling baby,
    converting the measured flow rate and pattern generated by the suckling baby to a suction power and pattern, and
    applying the suction power and pattern to the breast pump.

11. The method of claim 10 wherein converting the measured flow rate and pattern generated by the suckling baby is based on a predetermined conversion table.

12. The method of claim 10 further comprising creating the conversion table by:
    using a breast pump to generate flow through a tube at different vacuum powers and patterns,
    measuring the flow rate and pattern through the tube generated by the pump,
    creating a conversion table from flow rate and pattern through the tube to suction power and pattern of the pump.

* * * * *